United States Patent [19]

Sholder

[11] Patent Number: 4,974,589
[45] Date of Patent: Dec. 4, 1990

[54] AUTOMATICALLY ADJUSTABLE BLANKING PERIOD FOR IMPLANTABLE PACEMAKER

[75] Inventor: Jason A. Sholder, Northridge, Calif.

[73] Assignee: Siemens-Pacesetter, Inc., Sylmar, Calif.

[21] Appl. No.: 422,714

[22] Filed: Oct. 17, 1989

[51] Int. Cl.$^5$ .............................................. A61N 1/00
[52] U.S. Cl. ............................................ 128/419 PG
[58] Field of Search ................. 128/419 PG, 419 PT, 128/419 P

[56] References Cited

U.S. PATENT DOCUMENTS

| | | | |
|---|---|---|---|
| 4,462,407 | 7/1984 | Herscovici et al. | 128/419 PG |
| 4,470,418 | 9/1984 | Herscovici et al. | 128/419 PG |
| 4,686,988 | 8/1987 | Sholder | 128/419 PT |
| 4,712,555 | 12/1987 | Thornander et al. | 128/419 PG |
| 4,750,495 | 1/1988 | Moore et al. | 128/419 PG |
| 4,766,901 | 8/1988 | Callaghan | 128/419 PG |
| 4,788,980 | 12/1988 | Mann et al. | 128/419 PG |

OTHER PUBLICATIONS

Barold, et al., "Programmability in DDD Pacing," Pace, vol. 7, pp. 1159-1164 (Nov.-Dec. 1984).
Barold, et al., "Crosstalk Due to Activation of Atrial Sense Marker Function of DDD Pulse Generators," Pace, vol. 10, pp. 293-301 (Mar.-Apr. 1987).
Johnson, C. D., "Atrial Synchronous Ventricular Inhibited (VDD) Pacemaker-Mediated Arrhythmia Due to Atrial Undersensing and Atrial Lead Oversensing of Far-Field Ventricular Afterpotentials of Paced Beats: Crosstalk," Pace, vol. 9, pp. 710-719, (Sep.-Oct. 1986).
Kersschot, et al., "Atrial Pacing Bigeminy: A Manifestation of Crosstalk," Pace, vol. 8, pp. 402-407 (May--Jun. 1985).

Primary Examiner—Francis Jaworski
Assistant Examiner—George Manuel
Attorney, Agent, or Firm—Bryant R. Gold; Malcolm J. Romano; Lisa P. Weinberg

[57] ABSTRACT

An automatically adjustable blanking circuit and method of generating an adjustable blanking interval for use with a dual channel implantable pacemaker includes means for generating a basic blanking interval for a first channel of the pacemaker each time a stimulation pulse is generated on a second channel. The basic blanking interval includes a first absolute refractory portion and a second relative refractory portion. During the absolute refractory portion, the sensing circuits of the first channel are disabled. During the relative refractory portion, the sensing circuits of the first channel are enabled and any activity sensed in the first channel is considered to be crosstalk or noise and the basic blanking interval is retriggered. Retriggering of the basic blanking interval continues for so long as activity is sensed in the first channel during the relative refractory portion of each retriggered basic blanking interval, up to a maximum blanking interval. If no activity is sensed during the relative refractory portion of the basic blanking interval, the blanking interval ends, and the sensing circuits of the first channel thereafter monitor the first channel for spontaneous cardiac activity.

32 Claims, 7 Drawing Sheets

AUTOMATICALLY ADJUSTABLE BLANKING PERIOD FOR IMPLANTABLE PACEMAKER

BACKGROUND OF THE INVENTION

The present invention relates to implantable pacemakers, and more particularly to an automatically adjustable blanking circuit and method for use within a dual chamber implantable pacemaker. Such an adjustable blanking circuit automatically adjusts, during each pacemaker cycle, the blanking period of one channel of the pacemaker to avoid crosstalk from the other channel of the pacemaker.

A dual chamber pacemaker provides stimulation pulses to, and/or senses electrical activity in, both the atrium and ventricle of a heart. Such pacemakers utilize a lead having one or more electrodes for making electrical contact with each heart chamber (typically the right atrium or right ventricle). The same electrode advantageously serves as the medium for both stimulating the cardiac tissue and sensing cardiac activity (muscle contraction, or depolarization of muscle tissue, evidenced by an electrical signal) within that heart chamber. The circuits associated with a particular heart chamber, both for stimulating and sensing, are referred to as a channel. Thus, a dual chamber pacemaker includes two channels, one for providing stimulation pulses to and/or sensing electrical activity within the atrium, and the other for providing stimulation pulses to and/or sensing electrical activity within the ventricle.

Most modern pacemakers are programmable, allowing the operating mode of the pacemaker to be programmably set to a desired mode depending upon the particular needs of the patient. The operating mode is typically designated by a three letter code, where the first letter of the code indicates the chamber of the heart in which pacing occurs ("A"=atrium; "V"=ventricle; "D"=both the atrium and the ventricle); the second letter of the code indicates the chamber of the heart in which sensing occurs; and the third letter indicates the mode of response of the pacemaker ("T"=triggered; "I"=inhibited; "D"=double, i.e., atrial triggered and ventricular inhibited or atrial triggered/ inhibited and ventricular inhibited).

One operating mode for a dual chamber pacemaker, for example, is the DDD mode, wherein stimulation and sensing occur in both the atrium and ventricle, and wherein the response mode of the pacemaker may be either inhibited or triggered, as required. In such mode, the atrial channel senses whether a P-wave occurs (indicating contraction of the atrium) within a prescribed time period. If so, then an atrial stimulation pulse (hereafter an "A-pulse") is inhibited from being delivered to the atrium. If not, then the A-pulse is delivered to the atrium, thereby triggering an atrial contraction. Similarly, the ventricular channel senses whether an R-wave occurs (indicating contraction of the ventricle) within a prescribed time period. If so, then a ventricular stimulation pulse (hereafter a "V-pulse") is inhibited from being delivered to the ventricle. If not, then the V-pulse is delivered to the ventricle, thereby triggering a ventricular contraction. In this way, each chamber of the heart has a prescribed time period in which contraction should occur. If contraction does not occur within the prescribed time period, then stimulation pulses are delivered in order to trigger contraction. Such operation is termed "demand" pacing, because stimulation pulses are provided only on demand, that is, only as needed. In order for a dual chamber pacemaker to properly perform its function of providing stimulation pulses on demand, it is imperative that it be able to properly sense P-waves and R-waves. That which is sensed by the atrial channel is usually assumed to be a P-wave; and that which is sensed by the ventricular channel is usually assumed to be an R-wave. However, it is not uncommon for an A-pulse, or the P-wave resulting from an atrial contraction caused by an A-pulse, to couple over to the ventricular channel sensing circuits. Similarly, it is quite common for a V-pulse, or the R-wave resulting from a ventricular contraction caused by a V-pulse, to couple over to the atrial channel sensing circuits. Such cross coupling of an electrical signal from one channel of a dual channel pacemaker to the other channel is referred to as "crosstalk." Modern dual chamber pacemakers must utilize some means for handling crosstalk if reliable operation is to be maintained.

For example, after an A-pulse has been delivered to the heart, the atrial muscles contract, causing the desired atrial evoked response from the heart. However, accompanying such muscle contractions are electrical signals that may be sensed through crosstalk by the ventricular sensing circuits. If of sufficient magnitude, these crosstalk signals will be interpreted by the ventricular sensing circuits as spontaneous ventricular activity (e.g., an R-wave), when in fact no R-wave has occurred, thereby causing the pacemaker to inhibit the delivery of a V-pulse, even though such V-pulse may be needed.

The problem of crosstalk is discussed generally in, e.g., C. D. Johnson, "Atrial Synchronous Ventricular Inhibited (VDD) Pacemaker-Mediated Arrhythmia Due to Atrial Undersensing and Atrial Lead Oversensing of Far-Field Ventricular Afterpotentials of Paced Beats: Crosstalk", *Pace,* Vol. 9, pp. 710–19 (Sept.-Oct. 1986). A discussion of a particular type of crosstalk involving the generation of marker signals may be found in Barold et al., "Crosstalk Due to Activation of Atrial Sense Marker Function of DDD Pulse Generators," *Pace,* Vol. 10, pp. 293–301 (March-April 1987).

The most common technique used in dual chamber or two-channel pacemakers to deal with crosstalk is to utilize a "blanking period" or "blanking interval" in order to blank out or otherwise disable the sensing circuits of one channel immediately after a stimulation pulse has been delivered to the other channel. During the blanking period following delivery of an A-pulse on the atrial channel, for example, the ventricular sensing circuits of the ventricular channel are made absolute refractory (meaning that no sensing of any kind can occur). Hence, any crosstalk (or other noise) signals that occur during the blanking interval are not sensed. While various circuit arrangements are known in the art for effectuating a desired blanking interval, see, e.g., U.S. Pat. No. 4,462,407 (separate input/output circuits for each channel powered by respective isolated capacitors) and U.S. Pat. No. 4,470,418 (switched bipolar leads), the most common circuit arrangement is to simply disable the sensing circuit of one channel by removing power from the sensing amplifier of that channel during the blanking interval. A difficulty still remains, however, in determining the correct length of the blanking period.

In theory, the blanking interval or period associated with the ventricular channel should be made as short as possible in order to allow the ventricular sense circuits to sense ventricular activity (e.g., an R-wave) during as much of the A-V interval as possible. (The "A-V interval" is the maximum period allowed by the pacemaker between contraction of the atrium and contraction of the ventricle. The A-V interval commences with delivery of an A-pulse or the sensing of a P-wave, and lasts a prescribed time thereafter. During this prescribed time, an R-wave must be sensed in order to inhibit delivery of a V-pulse at the conclusion of the prescribed time.) On the other hand, the ventricular blanking period or interval should be made sufficiently long to effectively block out any residual crosstalk signals (resulting from the atrial contractions triggered by the A-pulse). Unfortunately, the optimum blanking interval for one patient may not be the optimum blanking interval for another patient, nor for even the same patient at different times. That is, if some of the basic pacemaker parameters are changed, or if other changes occur that somehow affect the manner in which the patient's heart responds to a stimulation pulse, the amount of crosstalk that occurs can be significantly altered. For example, a blanking interval of 13 msec may be sufficient for a programmed A-pulse amplitude of 2 volts; but a blanking interval of 50 msec may be needed if the A-pulse amplitude is increased to 7 volts. What is needed, therefore, is a reliable technique for making the blanking interval of one channel be as short as possible while at the same time having it be sufficiently long so as to prevent crosstalk detection of the stimulation pulse by the other channel.

Prior art approaches dealing with the aforementioned problem (of finding an optimum value for the blanking interval) have focused on making the blanking interval programmable. Siemens-Pacesetter, Inc. of Sylmar, Calif., for example, allows the ventricular blanking period in its AFP pacemaker to be programmed to 13, 25, 38 or 50 msec. See also, Barold et al, "Programmability in DDD Pacing," *Pace*, Vol. 7, pp. 1159-64 (Nov.-Dec. 1984), wherein the desirability of having a programmable blanking interval is suggested. A programmable blanking interval, however, is totally dependent upon skilled human intervention in order to assure that the correct value is chosen.

Further, because only a few blanking interval values are typically available from which to programmably choose a desired blanking interval value, the optimum blanking interval value for a particular patient will likely not be available. Moreover, even if the correct blanking interval value is available for use by a given patient at one particular time, this same blanking interval value may not be the correct value at a subsequent time. Changes made to other programmable parameters of the pacemaker, physiological changes within the patient, as well as the passage of time, can all influence the proper blanking interval value that should be used. Hence, what is needed is a technique for periodically adjusting the blanking interval value to an optimum value over a wide range of possible values without the need for highly skilled human intervention.

Because of the dependence of the correct blanking interval value on other programmable parameters of the pacemaker, it is known in the art to automatically change the programmed value of the blanking interval to a more appropriate value if another programmable parameter of the pacemaker is changed. See, e.g., Kersschot et al., "Atrial Pacing Bigeminy: A Manifestation of Crosstalk," *Pace*, Vol. 8, pp. 402-07 (May-June 1985), wherein it is suggested that the blanking interval value be automatically reprogrammed if the programmed values of the atrial output and/or ventricular sensitivity are changed. Hence, if either the A-pulse amplitude or width is reprogrammed, for example, such values can impact the optimum blanking interval value. Thus, it is known in the art to include in the programmer a table of correlated values, so that when certain key parameters of the pacemaker are reprogrammed, such as the A-pulse amplitude or width, an appropriate blanking period value associated with that key parameter is also automatically reprogrammed. Unfortunately, however, the values used in such "correlation tables" may not be valid for all conditions. That is, one correlation table may be needed at one heart rate, and another correlation table may be needed at another heart rate. Moreover, the cost and complexity of having to continually switch and update correlation tables can quickly overshadow the benefits derived from making the automatic reprogramming changes in the first place. Thus, what is clearly needed is a simple and inexpensive way to automatically adjust the blanking interval value to an optimum value for the patient regardless of the patient's heart rate or other factors that may create the need to change the optimum blanking interval value.

The present invention advantageously addresses the above and other needs.

SUMMARY OF THE INVENTION

The present invention is directed to an apparatus and method for automatically generating an adjustable blanking interval within a dual chamber implantable pacemaker. The adjustable blanking interval optimally sets the length of the blanking period of the pacemaker—that period during which the sensing circuits of one channel are disabled so as not to erroneously interpret crosstalk signals originating on the other channel as valid cardiac events—to a value that best rejects crosstalk and noise and yet still allows sufficient time for valid cardiac events to be sensed.

In accordance with the present invention, a basic blanking interval is triggered by the delivery of a stimulation pulse on a first channel, e.g., the atrial channel, of a dual chamber pacemaker. This basic blanking interval is divided into a first absolute refractory portion and a second relative refractory portion. During the first absolute refractory portion, no activity can be sensed on a second channel, e.g., the ventricular channel. During the second relative refractory portion, any activity sensed on the second channel is presumed to be crosstalk or noise and immediately causes the basic blanking interval to start over, i.e., to be retriggered. The restarting or retriggering of the basic blanking interval continues each time activity is sensed during the relative refractory portion of the basic blanking interval up to a programmable maximum prescribed time, termed the maximum blanking interval ("MBI"), subsequent to the generation of the stimulation pulse on the first channel. Advantageously, the MBI may be as long as the programmed interval between stimulation pulses, e.g., the programmed A-V interval (in the case of a ventricular blanking interval), or some interval that is less than the programmed interval between stimulation pulses. If no activity is sensed by the end of the relative refractory portion of the latest basic blanking interval (initial or retriggered), then the blanking interval is over, and the sensing circuits of the second channel are active thereafter up to the end of the programmed interval between stimulation pulses.

The total blanking interval resulting from the present invention thus comprises the sum or the initial basic blanking interval plus any retriggered basic blanking intervals. As indicated, the maximum value that the total blanking interval can assume is the programmed MBI. The blanking interval thus generated may differ in length with each delivery of a stimulation pulse on the other channel. That is, the total blanking interval is not fixed, as in the prior art devices, but is automatically adjusted after the delivery of each stimulation pulse as a function of the amount of crosstalk that occurs during each relative refractory portion of the initial basic blanking interval or any retriggered basic blanking intervals.

In one embodiment of the present invention, hereafter termed the "asynchronous embodiment," the absolute and relative refractory portions of the basic blanking interval, which portions combine to make up the basic blanking interval, may be programmably set to any desired values. In this embodiment, the total blanking interval comprises the sum of: (1) the initial absolute refractory portion; (2) that amount of the initial relative refractory portion up to the time activity is sensed, if any, to cause retriggering of the basic blanking interval; (3) the absolute refractory portions of any retriggered basic blanking intervals; and (4) that amount of the relative refractory portions of any retriggered basic blanking intervals up to the time activity is sensed, if any.

In another embodiment of the invention, hereafter termed the "synchronous embodiment", the basic blanking interval may be a prescribed integral number of clock cycles in length, with the absolute refractory portion comprising a fixed number of clock cycles in length, and the relative refractory portion comprising the remainder number of clock cycles in length (i.e., the difference between the prescribed integral number of clock cycles of the basic blanking interval and the fixed number of clock cycles of the absolute refractory portion). In this synchronous embodiment, the total blanking interval comprises an integral number of clock cycles, and is made up of the initial absolute refractory portion (a fixed number of clock cycles), any retriggered absolute refractory portions (each also comprising a fixed number of clock cycles), and a final relative refractory portion (also a fixed number of clock cycles). A preferred configuration of this synchronous embodiment uses a basic blanking interval of two clock cycles, with the absolute refractory portion comprising one clock cycle, and the relative refractory portion also comprising one clock cycle. In this preferred configuration, for example, if the basic blanking interval is retriggered four times, the total blanking interval is five clock cycles in length (four absolute refractory portions of one clock cycle each, and one relative refractory portion of one clock cycle).

The present invention may thus be characterized as a method of automatically generating an adjustable blanking interval in a dual channel pacemaker, the adjustable blanking interval being used by a first channel of the pacemaker to blank out electrical activity present in the first channel during the blanking interval, which electrical activity (if any) is more likely than not to be noise or crosstalk. This method includes the steps of: (a) generating a basic blanking interval in a first channel of the pacemaker whenever a stimulation pulse is generated in a second channel of the pacemaker, this basic blanking interval being divided into a first portion and a second portion; (b) disregarding any electrical activity present in the first channel during the first portion of the blanking interval; (c) retriggering the basic blanking interval in response to any electrical activity present in the first channel during the second portion of the basic blanking interval; (d) repeating steps (b) and (c) for so long as electrical activity is present in the first channel during the second portion of any retriggered basic blanking interval; and (e) making the adjustable blanking interval equal to a value that varies as a function of the number of basic blanking intervals retriggered in step (c).

The invention may further be characterized as a method of automatically generating an adjustable blanking period in a first prescribed channel of a dual chamber pacemaker that includes: (a) initiating a basic blanking interval in a first channel of the pacemaker coincident with the delivery of a stimulation pulse in a second channel, the basic blanking interval comprising a first fixed absolute refractory portion followed by a second relative refractory portion; (b) disabling the sensing means of the first channel during the first fixed absolute refractory portion of the basic blanking interval, whereby no electrical activity of any kind is sensed during the first fixed absolute refractory portion; (c) enabling the sensing means of the first channel during the second relative refractory portion of the blanking interval; (d) restarting the basic blanking interval in response to the first occurrence of any electrical activity sensed by the sensing means of the first channel during the second relative refractory portion, with the adjustable blanking period comprising the cumulative sum of the first basic blanking interval plus any restarted blanking intervals; and (e) terminating the adjustable blanking period in the first channel in response to the earliest occurrence of either (i) the conclusion of the second relative refractory portion without the occurrence of any sensed electrical activity to restart the basic blanking interval, or (ii) the conclusion of a prescribed maximum blanking period, where the prescribed maximum blanking period starts at the delivery of the stimulation pulse in the second channel.

Still further, one embodiment of the invention comprises apparatus for automatically generating an adjustable blanking interval in a dual chamber pacemaker, the dual chamber pacemaker including first and second channels in which electrical activity may be sensed, the adjustable blanking interval being used in the first channel to blank out electrical activity sensed in the first channel that may be noise or crosstalk originating in the second channel. Such apparatus includes: (a) generating means for generating a basic blanking interval in the first channel whenever a stimulation pulse is generated in the second channel, this generating means dividing the basic blanking interval into a first portion and a second portion; (b) first circuit means for disregarding any electrical activity present in the first channel during the first portion of the blanking interval; (b) second circuit means for retriggering the basic blanking interval in response to any electrical activity present in the first channel during the second portion of the basic blanking interval; and (c) third circuit means for making the adjustable blanking interval equal to a value that varies as a function of the number of basic blanking intervals retriggered by the second circuit means.

Another embodiment of the invention is directed to an implantable dual chamber pacemaker that includes: (a) first and second channels for allowing electrical contact to be made with first and second chambers of a heart, respectively; (b) pacemaker control logic for generating a trigger signal when a stimulation pulse is to be presented on one of these channels., (c) sensing means for sensing electrical activity that occurs on the other channel; and (d) blanking interval means responsive to the trigger signal and the sensing means for automatically generating an adjustable blanking signal pulse that has a variable width, the adjustable blanking signal pulse commencing at a time determined by the trigger signal and ending at a time determined by the sensing means. The adjustable blanking signal pulse thus generated is used to reject any electrical activity sensed by the sensing means when the blanking signal pulse is present, and to accept any electrical activity sensed by the sensing means when the blanking signal pulse is absent.

It is a feature of the present invention to provide a blanking interval generation circuit for use with a dual chamber implantable pacemaker that automatically adjusts the blanking interval value of a particular channel of the pacemaker to an optimum value without the need of skilled human intervention.

It is another feature of the present invention to provide such a blanking interval generation circuit that makes the automatic adjustment of the blanking interval value on a regular basis, thereby making the circuit fully responsive to changes in the patient, or changes in the programming of the patient's pacemaker, that may dictate a need for a change in the blanking interval value.

It is yet another feature of the present invention to update the blanking interval value of one channel of the pacemaker after the delivery of each stimulation pulse on the other channel of the pacemaker.

It is still another feature of the present invention to provide an automatically adjustable blanking interval generation circuit that is low in cost, simple to fabricate, and non-complex to operate.

Yet a further feature of the present invention provides a method of automatically generating an adjustable blanking interval in a dual chamber pacemaker to an optimum value that both minimizes crosstalk between channels of the pacemaker and yet allows the sensing functions of the particular channel of interest to serve their intended purpose.

BRIEF DESCRIPTION OF THE DRAWINGS

The above and other aspects, advantages and features of the present invention will be more apparent from the following more particular description thereof, presented in conjunction with the following drawings, wherein.

DETAILED DESCRIPTION OF THE INVENTION

Figure 1A:
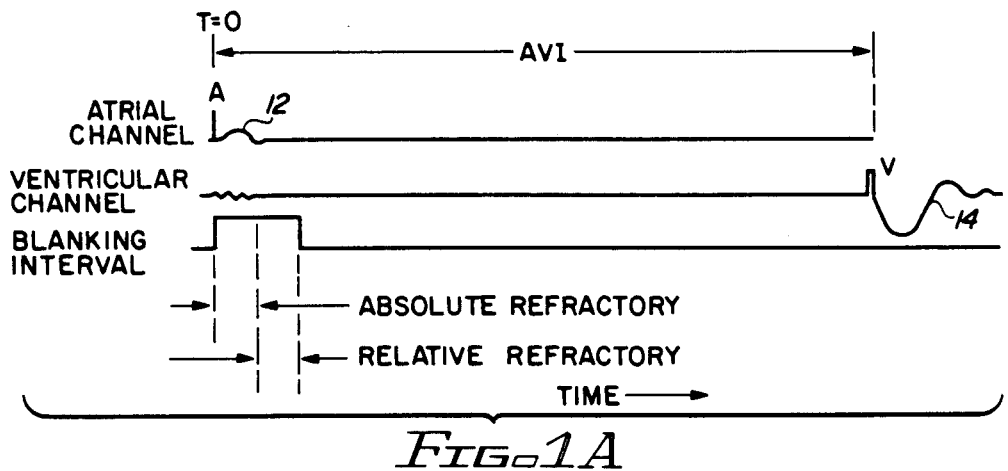
FIGS. 1A and 1B are timing diagrams illustrating the manner in which an adjustable blanking period is generated in accordance with an synchronous embodiment of the present invention.
Figure 1B:
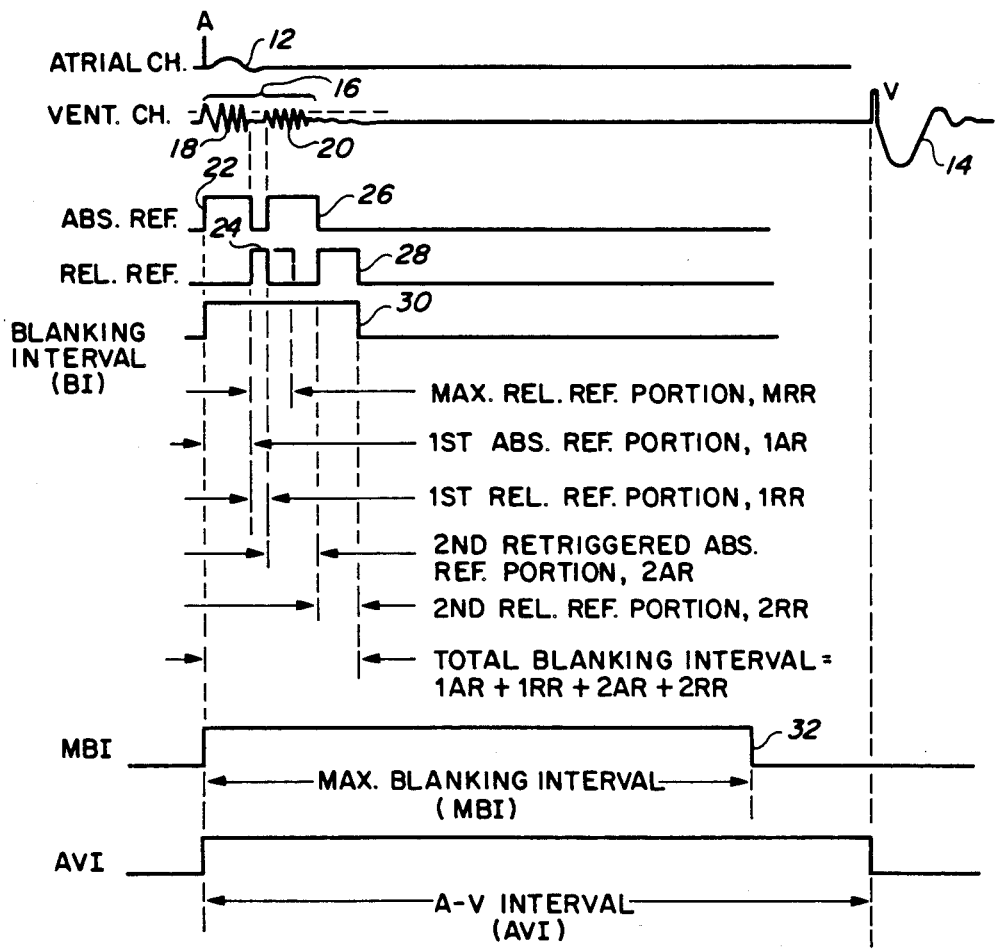

The following description is of the best mode presently contemplated of practicing the invention. This description is not to be taken in a limiting sense, but is made merely for the purpose of describing the general principles of the invention. The scope of the invention should be ascertained with reference to the appended claims. Referring first to FIGS. 1A and 1B, timing diagrams are shown illustrating the manner in which an adjustable blanking period is generated in accordance with an asynchronous embodiment of the invention. By "asynchronous", it is meant that the blanking interval does not assume a fixed length, and is not synchronized with any clock signals that may be used within the pacemaker; but is rather triggered by the generation of a stimulated pulse on one channel of the pacemaker, and continues for an adjustable time thereafter, that varies as a function of the noise or crosstalk that is present, in the manner explained below.

FIG. 1A illustrates the operation of the asynchronous embodiment of the invention for the situation where there is no crosstalk. Referring to FIG. 1A, the top line indicates the signals that may appear on the atrial channel of the pacemaker, while the middle line illustrates the signals that may be present on the ventricular channel of the pacemaker. The bottom line shows the blanking interval that is generated in accordance with the apparatus and method of the present invention. As seen in FIG. 1A, the atrial channel has an atrial stimulation pulse, A, that is generated at time t=0. The atrial pulse A invokes a P-wave 12 on the atrial channel. At the time that the A-pulse is generated on the atrial channel, only a small signal, shown as a ripple, appears on the ventricular channel. In many situations, this small signal will not be sufficiently large to be of any consequence. i.e., there will be no crosstalk.

Coincident with the generation of the A-pulse, the blanking interval begins. This blanking interval is made up of two portions: a first absolute refractory portion, and a second relative refractory portion. In the absence of any noise or crosstalk on the ventricular channel, as shown in FIG. 1A, the blanking interval includes only the absolute refractory portion and the relative refractory portion, as shown in FIG. 1A.

As will be explained more fully below, during the absolute refractory portion of the blanking interval, the sensing circuits of the ventricular channel are disabled and are unable to sense any activity. During the relative refractory portion, on the other hand, the sensing circuits of the ventricular channel are enabled, but the response of the pacemaker to sensing any activity during the relative refractory portion is different than the response of the pacemaker to sensing activity on the ventricular channel after the blanking interval. It is, of course, the function of the blanking interval to block out or otherwise prevent any signal occurring during the time period defined by the blanking interval from being interpreted by the pacemaker circuits as a cardiac event, such as an R-wave (indicating contraction of the ventricle). Accordingly, if cardiac activity is sensed during the relative refractory portion of the blanking interval, such activity is presumed to be noise or crosstalk. If such occurs, then in accordance with the present invention, the blanking interval is automatically increased in length. If no activity is sensed during the relative refractory portion, however, as shown in FIG. 1A, then the blanking interval terminates, and the sensing circuits on the ventricular channel are thereafter enabled and any activity sensed is presumed to be a valid cardiac event, e.g., an R-wave.

Still referring to FIG. 1A, it is seen that at a prescribed time after the generation of the A-pulse of the atrial channel, a V-pulse is generated on the ventricular channel, invoking an R-wave 14 thereon. The time interval between the A-pulse and the V-pulse is commonly referred to as the A-V interval, or AVI, and represents a programmed value of the pacemaker. After the blanking interval pulse terminates, the sensing circuits of the ventricular channel are enabled, and any activity sensed on the ventricular channel is presumed to be an R-wave, indicating that the ventricle has contracted. If the ventricle does not contract before the termination of the A-V interval, then the V-pulse is generated by the pacemaker, as shown in FIG. 1A.

Referring next to FIG. 1B, the timing waveform diagram is shown similar to that of FIG. 1A, except that some noise or crosstalk 16 appears and remains on the ventricular channel at the time that the A-pulse is generated on the atrial channel. As with FIG. 1A, the generation of the A-pulse begins the first portion of the blanking interval, the absolute refractory portion. This absolute refractory portion is shown in FIG. 1B as a pulse 22, having a fixed width, "1AR" (for first absolute refractory). The termination of the first absolute refractory pulse 22 triggers the generation of a relative refractory pulse 24. This relative refractory pulse has a maximum width labeled "MRR" (for maximum relative refractory). However, as indicated in FIG. 1B, the noise or crosstalk 16 appearing in the ventricular channel has not completely terminated during the relative refractory portion of the blanking interval. In particular, a burst of noise or crosstalk 20 is present during this relative refractory portion. The occurrence of this noise or crosstalk 20 causes the relative refractory portion 22 to be cut short, that is, to terminate prior to the maximum time permitted by the maximum relative refractory portion; and causes the absolute refractory pulse to again be triggered. This retriggering of the absolute refractory pulse is illustrated in FIG. 1B as a second absolute refractory pulse 26. This retriggered absolute refractory pulse 26 has a duration or width the same as the first absolute refractory pulse 22.

At the conclusion of the second absolute refractory pulse 26, a second relative refractory pulse 28 is generated. This second relative refractory pulse 28 continues for a prescribed time, MRR, at which time the pulse terminates. Because the noise or crosstalk on the ventricular channel no longer exists during the second relative refractory pulse 28, there is no further retriggering of the absolute refractory pulse. Thus, in accordance with the teachings of the present invention, a blanking interval (BI) pulse 30 is generated that begins with the first triggering of the first absolute refractory pulse 22 and terminates at the conclusion of the last retriggered relative refractory pulse 28. That is, as seen in FIG. 1B, the blanking interval pulse 30 has a width that comprises the cumulative sum of the first absolute refractory pulse 22, or 1AR; the first relative refractory pulse 24 (which is a shortened pulse, and is therefore labeled "1RR"), the second absolute refractory pulse 26, 2AR; and the second relative refractory pulse 28, 2RR.

Further shown in FIG. 1B is a maximum blanking interval pulse 32. This maximum blanking interval (MBI) pulse defines the maximum time or width that the blanking interval pulse 30 may assume. That is, in the event that noise or crosstalk continues to occur on the ventricular channel, the blanking interval pulse continues to automatically adjust in length through the process described above (retriggering of the absolute refractory pulse followed by the relative refractory pulse). However, in order to prevent the blanking interval pulse from extending for an undesirably long period of time, the present invention limits the blanking interval pulse 30 to assume a value that is the shorter of the maximum blanking interval pulse 32, or the cumulative sum of the absolute refractory pulse 22, the relative refractory pulse 24, and any retriggered absolute refractory pulses or relative refractory pulses.

It is contemplated that the maximum blanking interval pulse 32 be a programmable value that can assume any value up to the A-V interval, or some value less than the A-V interval. For demand pacer operation, it is desirable that at least one portion of the A-V interval be nonrefractory, in which case the MBI would be programmed to be a prescribed amount less than the AVI. Nonetheless, for some patients in some circumstances, it may be desirable to render the ventricular sensing circuits refractory during the entire A-V interval, in which case a V-pulse would always follow an A-pulse at the prescribed A-V interval thereafter.

As indicated in FIG. 1B, and as described above, the total length of the blanking interval pulse 30 is the cumulative sum of the various absolute refractory pulses and relative refractory pulses that are initially generated or subsequently retriggered. All but the last of the retriggered relative refractory pulses (that follow the retriggered absolute refractory pulses), will be shorter than their maximum length, depending upon when the crosstalk occurs within such relative refractory pulses. Hence, the length of the blanking interval pulse 30 (assuming a length less than the MBI) is not known in advance. For this reason, this embodiment is referred to as an asynchronous embodiment, meaning that the blanking interval pulse 30 assumes a length that is entirely a function of the noise or crosstalk that occurs on the ventricular channel.

Figure 2A:
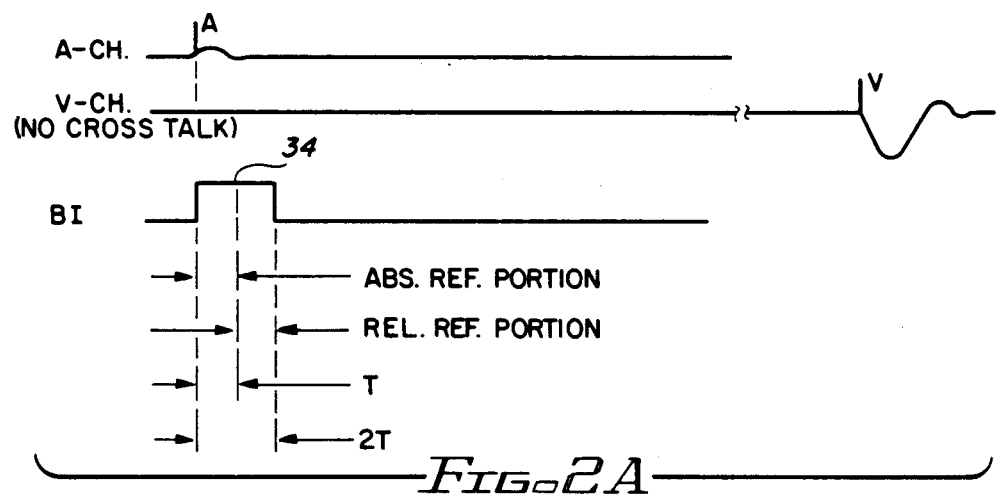
FIGS. 2A, 2B and 2C are timing diagrams illustrating the manner in which an adjustable blanking period is generated in accordance with a synchronous embodiment of the present invention.
Figure 2B:
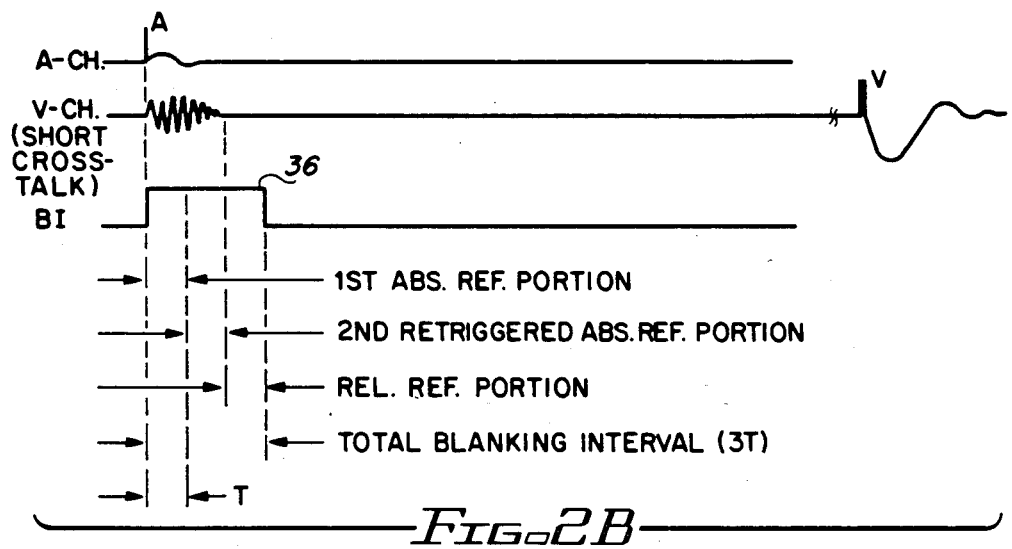
Figure 2C:
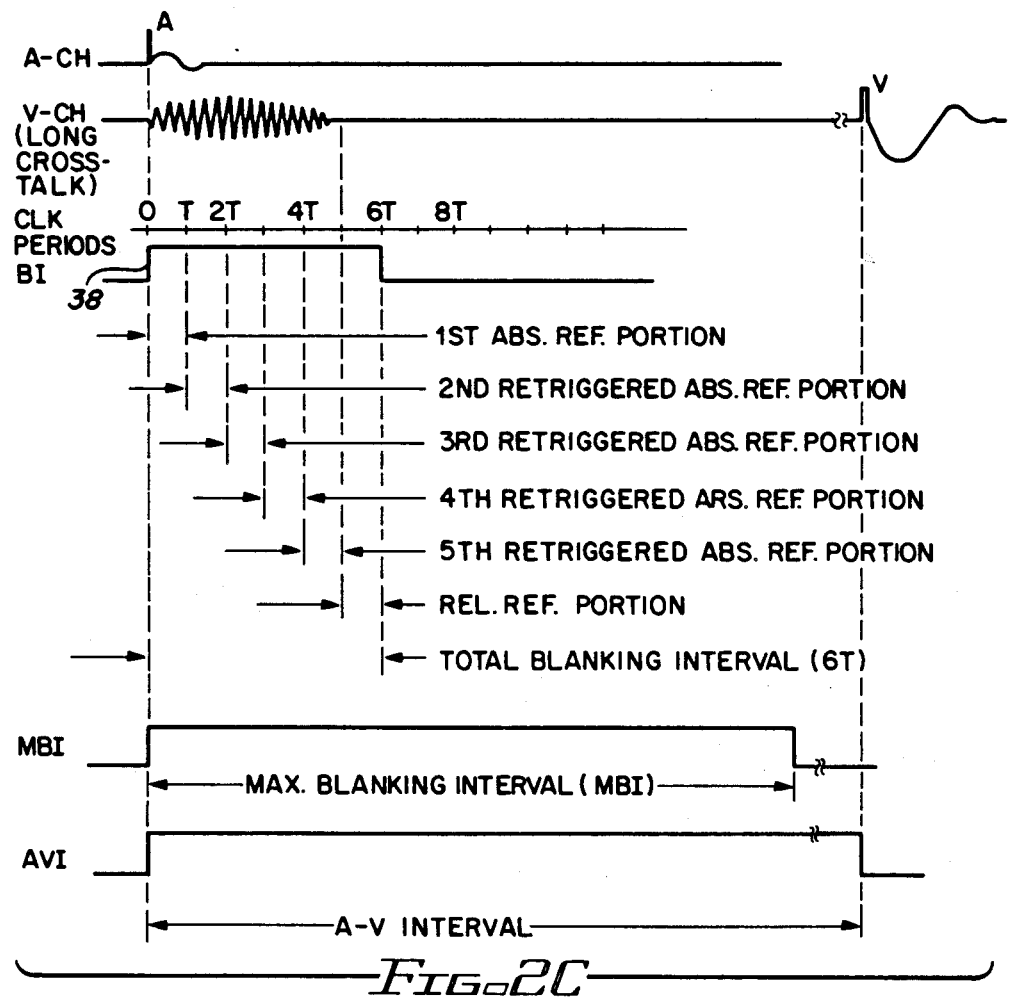

In contrast to the asynchronous approach illustrated in FIGS. 1A and 1B, FIGS. 2A, 2B, and 2C illustrate timing diagrams showing the manner in which an adjustable blanking period is generated in accordance with a synchronous embodiment of the present invention. The embodiment of the invention shown in FIGS. 2A, 2B and 2C is termed "synchronous" because the adjustable blanking interval generated is always an integral number of clock periods, T, in length. For example, in FIG. 2A, which illustrates a situation where there is no noise or crosstalk on the ventricular channel, the delivery of an A-pulse on the atrial channel initiates a blanking interval pulse 34. This blanking interval pulse is divided into a first absolute refractory portion and a second relative refractory portion, where each portion has a length T. Thus, because there is no crosstalk on the ventricular channel, and therefore nothing to retrigger the absolute refractory portion, the total length of the blanking interval pulse 34 is 2T.

In contrast, in FIG. 2B, a situation is illustrated wherein there is a short burst of noise or crosstalk appearing on the ventricular channel subsequent to the delivery of an A-pulse (stimulation pulse) on the atrial channel. As with all embodiments of the present invention, the delivery of the A-pulse on the atrial channel initiates the first absolute refractory portion of a blanking interval pulse 36. This first absolute refractory portion has a width or length T, the period of the clock signal that is used to generate the blanking interval pulse. After the termination of the first absolute refractory portion, the relative refractory portion begins However, crosstalk or noise is present on the ventricular channel at this time. Therefore, at the conclusion of the first absolute refractory portion (and therefore at the beginning of the subsequent relative refractory portion), a second absolute refractory portion is immediately retriggered. At the conclusion of the second retriggered absolute refractory portion, the noise or crosstalk on the ventricular channel has subsided, and the relative refractory portion, also having a length T, ends. Because no further noise or crosstalk appears on the ventricular channel during the relative refractory portion following the second retriggered absolute refractory portion, the blanking interval terminates, having a total length of 3T.

In FIG. 2C, another timing diagram of the present invention is illustrated for the situation where a long period of noise or crosstalk is present on the ventricular channel. As with the other embodiments, the delivery of an A-pulse on the atrial channel initiates a first absolute refractory portion of a blanking interval pulse 38. During this first absolute refractory portion, the noise or crosstalk appearing on the ventricular channel is of no consequence, as the sensing circuits are refractory during this time and unable to sense any activity. This first absolute refractory portion has a length T. At the conclusion of the first absolute refractory portion, the noise or crosstalk is still present on the ventricular channel, thereby triggering a second absolute refractory portion, also having a length T. At the conclusion of the second retriggered absolute refractory portion, the noise or crosstalk is still present on the ventricular channel, thereby retriggering a third absolute refractory portion of length T. At the conclusion of the third retriggered absolute refractory portion, the crosstalk still exists on the ventricular channel, thereby retriggering a fourth absolute refractory portion of length T. At the conclusion of this fourth retriggered absolute refractory portion, the crosstalk or noise still persists on the ventricular channel, thereby retriggering a fifth absolute refractory portion of length T. At the conclusion of the fifth retriggered absolute refractory portion, the noise or crosstalk on the ventricular channel has finally subsided, thereby initiating a relative refractory portion of the blanking interval pulse. Because no further noise or crosstalk appears on the ventricular channel during the relative refractory portion, which also has a length T, the blanking interval pulse 38 terminates at the conclusion of the relative refractory portion. Hence as seen in FIG. 2C, the blanking interval pulse 38 has a total length of 6 clock periods, or 6T, comprising a first absolute refractory portion, a second retriggered absolute refractory portion, a third retriggered absolute refractory portion, a fourth retriggered absolute refractory portion, a fifth retriggered absolute refractory portion, and a final relative refractory portion.

Also included in FIG. 2C is a maximum blanking interval pulse, or MBI. As previously described, should the extension of the blanking interval pulse exceed the maximum blanking interval pulse, MBI, then the logic circuitry used to generate the blanking interval pulse causes the blanking interval pulse to equal the maximum blanking interval pulse. In other words, the logic circuitry used to generate the adjustable blanking interval pulse in accordance with the present invention causes the blanking interval pulse to be equal to the shorter of either the maximum blanking interval pulse (MBI) or the sum of the first absolute refractory portion, any retriggered absolute refractory portions, and a final relative refractory portion.

As with the asynchronous embodiment, the maximum blanking interval is a programmed value that is typically set to some value less than the A-V interval, AVI. At a maximum, the MBI could be equal to the AVI if no sensing on the ventricular channel were needed for a particular patient. However, as has been indicated, for most patients, the MBI would be programmably set to some increment or value less than the A-V interval, thereby providing some period of time during the A-V interval during which the sensing circuits of the ventricular channel are enabled to sense ventricular activity.

Figure 3:
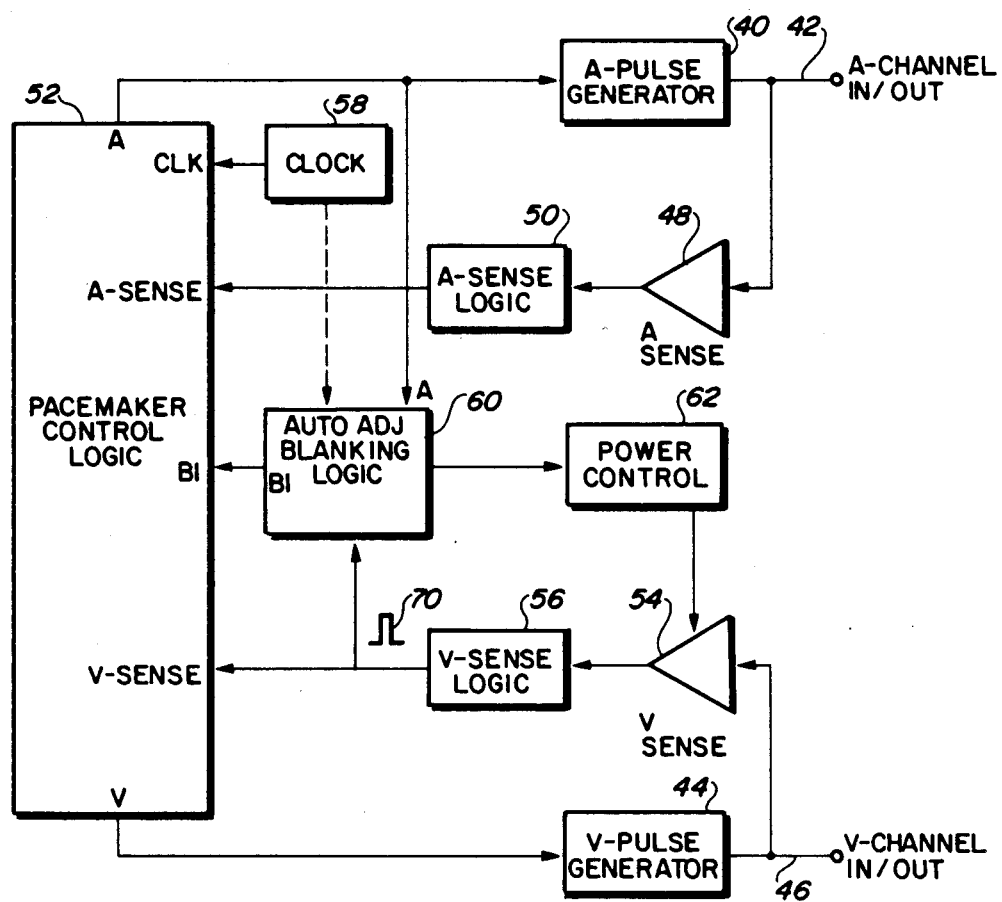
FIG. 3 is a block diagram of a dual chamber implantable pacemaker that includes automatically adjustable blanking logic in accordance with the present invention.

Referring next to FIG. 3, a block diagram of a dual chamber implantable pacemaker that includes the automatically adjustable blanking logic in accordance with the present invention is illustrated. This pacemaker includes an atrial generator 40 for generating atrial stimulation pulses (A-pulse) on an atrial channel 42. Similarly, a V-pulse generator 44 generates V-pulses for delivery to the ventricle over a second ventricular channel 46. Coupled to the atrial channel 42 is an atrial sense amplifier 48, the output of which is directed to A-sense logic 50. The function of the A-sense logic 50 is to generate an appropriate logic signal(s) for delivery to the pacemaker control logic 52. Similarly, coupled to the ventricular channel 46 is a ventricular sense amplifier 54. The output of the ventricular sense amplifier 54 is directed to V-Sense logic circuitry 56. The function of the V-Sense logic 56 is to generate the appropriate logic signal(s) for delivery to the pacemaker control logic 52 indicating that activity has been sensed on the ventricular channel 46. Clock circuitry 58 generates an appropriate clock signal that is also directed to the pacemaker control logic 52.

In accordance with conventional pacemaker operation, the pacemaker control logic 52, utilizing a clock signal generated by the clock circuitry 58, generates appropriate timing intervals, such as the A-V interval, during which the outputs of the A-sense logic 50 and/or the V-sense logic 56 are monitored in order to determine if appropriate activity is sensed on the respective atrial and ventricular channels. For example, if the pacemaker control logic 52 determines that no atrial activity has occurred, as determined by monitoring the A-sense input from the A-sense logic 50, within a prescribed time period, then an appropriate trigger signal is generated, identified as "A" in FIG. 3, for delivery to the A-pulse generator 40. This trigger signal A causes an A-pulse to be generated and delivered on the A-channel. If activity is sensed on the atrial channel within the prescribed time period, then the A trigger signal is not generated, and delivery of the A-pulse on the atrial channel is thereby inhibited.

Similarly, if after an appropriate period of time subsequent to the delivery of an A-pulse, or the sensing of atrial activity, the pacemaker control logic 52 determines that no activity has occurred in the ventricular channel 46 (which activity would indicate that the monitored ventricle has contracted), as determined by monitoring the V-sense input from the V-sense logic 56, within another prescribed time period (the AV interval), then another trigger signal is generated, identified as "V" in FIG. 3. The trigger signal V is delivered to the V-pulse generator 44, thereby causing a V-pulse to be generated and presented on the ventricular channel 46. If, on the other hand, activity is sensed on the ventricular channel within the prescribed AV interval, then the delivery of the V-trigger signal is inhibited. In this manner, the pacemaker control logic 52 delivers appropriate trigger pulses to the A-pulse generator 40 or the V-pulse generator 44, on demand, thereby maintaining a desired cardiac rhythm for the heart with which the pacemaker is used.

In accordance with the present invention, automatically adjustable blanking logic circuitry 60 generates a blanking interval (BI) pulse that defines when activity sensed on the ventricular channel should be interpreted as an R-wave and when it should be interpreted as crosstalk. This blanking interval pulse is presented to the pacemaker control logic, where it is used as described above in either FIGS. 1A-1B or 2A-2C. In the asynchronous embodiment of the invention (FIGS. 1A-1B), no clock signal is required within the adjustable blanking logic circuitry 60. However, within the synchronous embodiment of the invention, a clock signal would be delivered to the adjustable blanking logic circuitry 60 from the clock circuitry 58. The A trigger pulse delivered to the A-pulse generator 40 is also connected to the adjustable blanking logic circuit 60. It is this pulse, as explained above in the timing waveform diagrams of FIGS. 1A-1B and 2A-2C that triggers the beginning of the blanking interval pulse.

Still referring to FIG. 3, the absolute refractory portions of the blanking interval pulse, or signal, which absolute refractory portion is identified as a signal "AR" in FIG. 3, is presented to a power control circuit 62 so as to selectively enable or disable the V-sense amplifier 54. Thus, during the absolute refractory portions of the blanking interval pulse, when the AR signal is present, the power control circuit 62 removes power from the V-sense amplifier 54, thereby rendering the ventricular channel refractory during this period of time. During the relative refractory portions of the blanking interval pulse, the power control circuit 62 enables the V-sense amplifier 54, thereby allowing the V-sense amplifier 54 to sense activity occurring on the ventricular channel 46. However, any activity sensed during this time, as determined by monitoring the output of the V-sense logic 56 (which is also directed to the adjustable blanking logic circuitry 60), is interpreted as noise or crosstalk. The occurrence of such noise or crosstalk retriggers the absolute refractory portion of the blanking interval pulse in the manner described above.

It should be noted that the embodiment shown in FIG. 3 includes automatically adjustable blanking logic circuitry 60 that is adapted for use with the ventricular channel, as initiated by a stimulation pulse provided on the atrial channel. However, it is to be understood that the invention is not so limited, and that similar automatically adjustable blanking logic circuitry could be used on the atrial channel as well. In accordance with such an embodiment, a stimulation pulse (V-pulse) provided on the ventricular channel could also initiate an atrial channel blanking interval pulse that is divided into absolute and relative refractory portions. During the absolute refractory portions, no activity could be sensed on the atrial channel by the A-sense amplifier 48. During relative refractory portions, any activity sensed on the atrial channel would be interpreted as crosstalk or noise, thereby retriggering the absolute refractory portion of the blanking interval pulse. Only after the relative refractory portion of the blanking interval pulse had terminated, could the activity sensed on the atrial channel be interpreted as a valid atrial event (e.g., a P-wave).

Figure 4A:
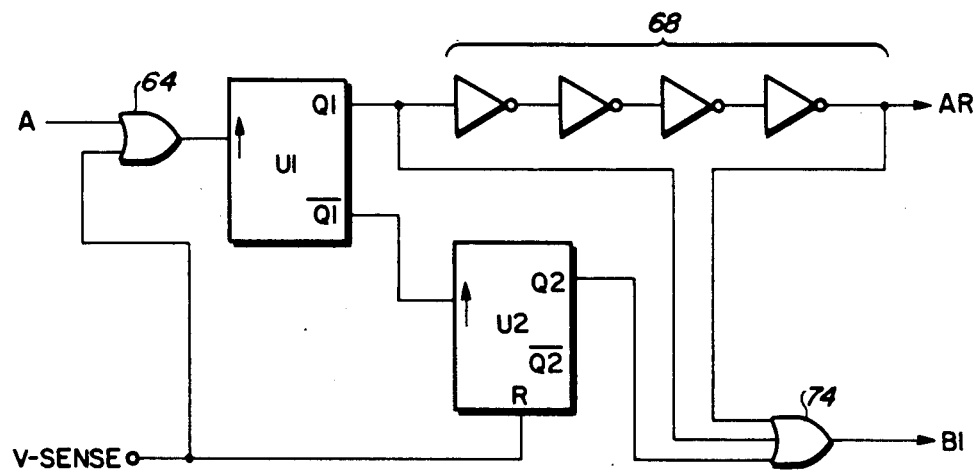
FIG. 4A illustrates a functional logic diagram of an asynchronous embodiment of the automatically adjustable blanking logic of FIG. 3.
Figure 4B:
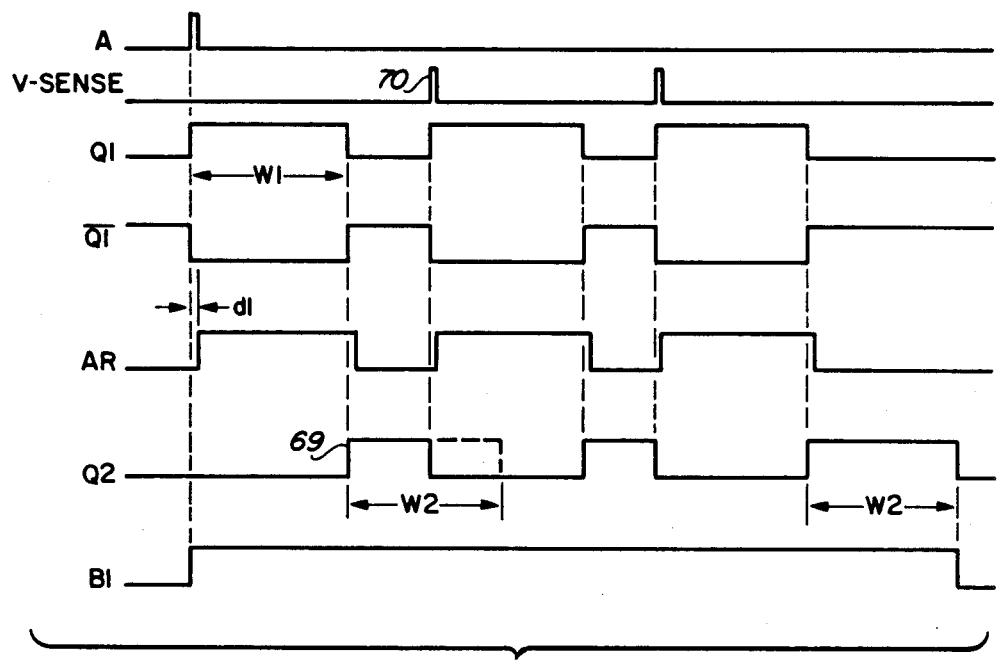
FIG. 4B is a timing waveform diagram illustrating the operation of the asynchronous circuit of FIG. 4A.

Turning next to FIG. 4A, a simplified functional logic schematic diagram of the asynchronous embodiment of the present invention is shown. FIG. 4B illustrates a timing waveform diagram associated with the operation of the circuit of FIG. 4A. As shown in FIG. 4A, the trigger pulse, A, is presented to one input of a two input OR gate 64. The output of the OR gate 64 is directed to a first one-shot circuit U1. This one-shot circuit U1 generates a pulse having a fixed length upon the occurrence of a positive transition of the input signal. Hence, as seen in FIG. 4B, the positive edge of the A trigger signal causes the output of the one-shot U1, identified as Q1, to generate a pulse 66 having width W1. This pulse 66 comprises the absolute refractory portion of the blanking interval pulse generated by the circuit of FIG. 4A. The Q1 output of the one-shot U1 passes through a series of invertor gates 68 with the output of the last gate providing the absolute refractory signal, AR. These gates 68 cause a slight delay from the time when the absolute refractory signal AR begins and the time the A trigger pulse was first generated. This slight delay is illustrated in FIG. 4B as the time d1. The inverted output of the first one-shot U1 is used to trigger a second one-shot U2. This second one-shot U2 generates the relative refractory portion of the blanking interval pulse. The trailing edge of the refractory pulse 66 thus triggers the one-shot U2, which one-shot generates another pulse 68 appearing at its Q2 output. The pulse 68 has a width W2. However, if prior to the termination of the relative refractory pulse 68, a pulse 70 appears at the output of the V-sense logic 56, indicating that activity has been sensed on the ventricular channel, the one-shot U2 is reset. This pulse 70 also passes through the OR gate 64 to cause the first one-shot U1 to be retriggered, thereby restarting the absolute refractory pulse 66. The total blanking interval pulse is the sum of the output of the first one-shot U1, the delayed output of the first one-shot U1, and the output of the second one-shot U2, as combined in a three-input OR gate 74. The introduction of the delay d1 in the absolute refractory portion of the pulse assures that the blanking interval pulse BI stays high during the entire period during which either the absolute refractory one-shot U1 or the relative refractory one-shot U2 is triggered.

As thus seen in FIG. 4B, the blanking interval pulse BI comprises the sum of the refractory pulses 66, each having a width W1, as well as the relative refractory pulses 69, each of which may have a variable length depending upon when the V-sense pulse 70 occurs, except for the last relative refractory pulse, which has a length of W2.

Figure 5A:
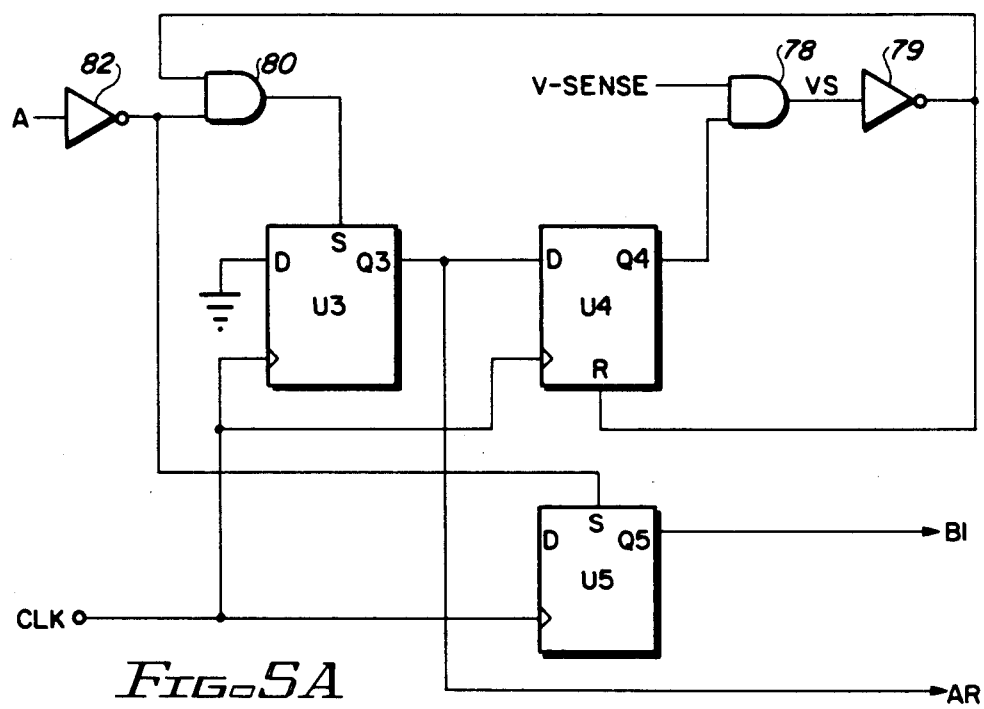
FIG. 5A depicts a functional logic diagram of a synchronous embodiment of the automatically adjustable blanking logic of FIG. 3.
Figure 5B:
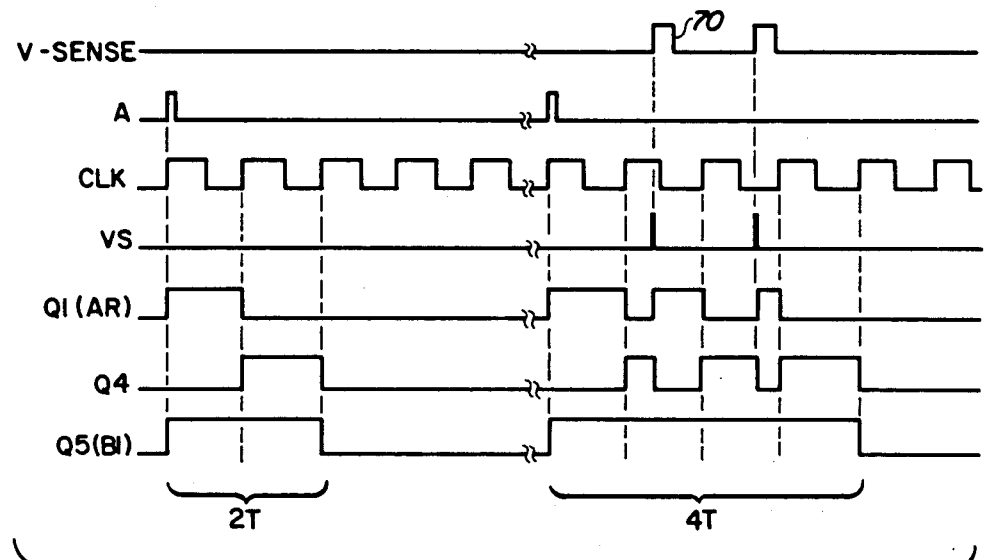
FIG. 5B is a timing waveform diagram illustrating the operation of the synchronous circuit of FIG. 5A.

FIG. 5A illustrates a simplified functional logic diagram for a synchronous embodiment of the present invention, with FIG. 5B illustrating a timing waveform diagram that illustrates the operation of the circuit of FIG. 5A. The synchronous circuit of FIG. 5A includes 3 D-type flip-flops, U3, U4 and U5. Flip-flops U3 and U4 function as a shift register with flip-flop U3 normally being set to the zero state at each positive-going transition of the clock signal, CLK. Flip-flop U5 functions as a latch circuit which generates the blanking interval pulse BI. The occurrence of a trigger pulse, A, causes the flip-flop U3 to be set to the one state. (It is assumed that the A trigger pulse A is already synchronized with the clock signal CLK, which is the normal case for a conventional pacemaker. However, equivalent circuits could readily be fashioned by those skilled in the art that perform this same function even though the A trigger pulse may not be synchronized with the clock signal CLK.) Flip-flop U3 remains set for one clock period, at which time flip-flop U4 is set by the shift-register action of the two flip-flops. Flip-flop U4 likewise remains set for one clock period. If no activity is sensed on the ventricular channel during the time that the flip-flop U4 is set, as is the case for the left-hand portion of FIG. 5B, a blanking interval pulse is generated by the flip-flop U5 having a total length of 2T, or 2 clock periods.

In the event that ventricular activity is sensed on the ventricular channel during the time that flip-flop U4 is set, as indicated for example by the pulse 70 appearing on the V-pulse sense line of FIG. 5B, such activity causes flip-flop U3 to again be set. This action occurs as follows: During the time that flip-flop U4 is set, an AND gate 78 is enabled, thereby allowing the V-sense pulse 70 to pass therethrough. The output of the AND gate is identified in FIGS. 5A and 5B as the signal "VS". The signal VS is routed through an invertor gate 79 to one input of another AND gate 80. The other input to the AND gate 80 is the A trigger pulse after such has been inverted by an invertor gate 82. The output of the AND gate 80, as shown in FIG. 5A, is coupled to the set input of flip-flop U3. Thus, whenever an A trigger pulse occurs, or whenever a V-sense pulse occurs when flip-flop U4 is set, the flip-flop U3 is set. The occurrence of the VS signal, as also shown in FIGS. 5A and 5B, is used to reset the flip-flop U4. The resetting of flip-flop U4 disables the AND gate 78, thereby causing the signal VS to be a very narrow "sliver" of a pulse having a duration determined largely by the propagation delay times of the gates 78, 79, and the reaction time of the flip-flop U4.

The setting of flip-flop U3 restarts the absolute refractory pulse, and the above-described process repeats. The flip-flop U3 remains set until the beginning of the next clock period, at which time the flip-flop U4 is set. Flip-flop U4 remains set for one clock period, or until activity is sensed on the ventricular channel, as evidenced by the presence of a pulse 70, whichever occurs first. Thus, as shown in FIG. 5B, where activity is sensed on the ventricular channel two times during the time that the relative refractory flip-flop U4 is set, the absolute refractory flip-flop U3 is set a total of three times, once by the initial A trigger signal A, and twice by the occurrence of each V-sense pulse 70. Thus, the total blanking interval pulse comprises a pulse having a length equal to four clock periods, or 4T.

Figure 6A:
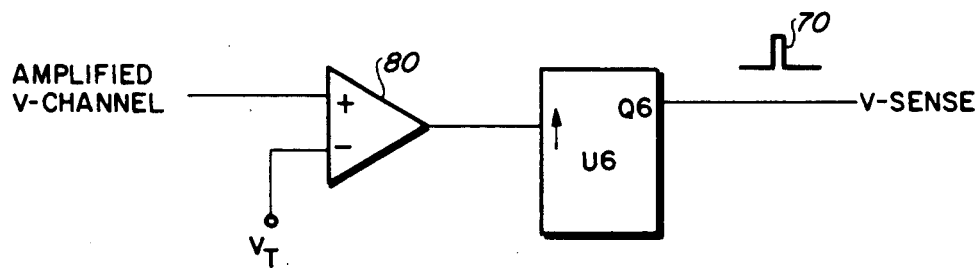
FIG. 6A is a schematic diagram of one embodiment of the V-Sense Logic of FIG. 3.
Figure 6B:
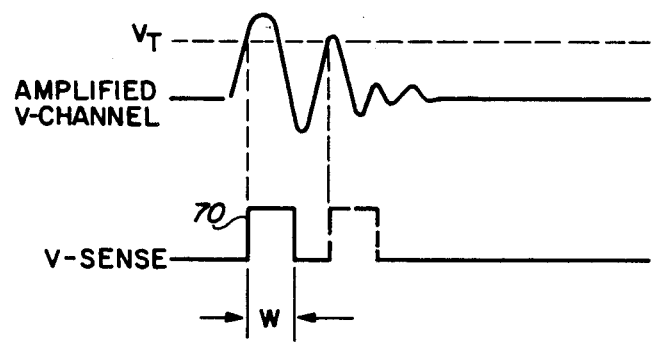
FIG. 6B is a timing waveform diagram illustrating the operation of the circuit of FIG. 6A.

FIG. 6A depicts a simplified functional logic diagram of one embodiment of the V-sense logic 56 of FIG. 3. In accordance with this embodiment, the output from the V-sense amplifier 54 is coupled to one input of a comparator circuit 80. The other input of the comparator circuit 80 is coupled to a threshold reference voltage $V_T$. The output of the comparator circuit is connected to the positive transition input of a one-shot U6, having an output Q6 that comprises the V-sense signal 70. Thus, in operation, as indicated in FIG. 6B, whenever the signal on the V-channel, as amplified by the V-sense amplifier 54, exceeds the threshold $V_T$, a pulse appears on the V-sense line. As indicated in FIG. 6B, this pulse has a width w, although it is to be understood that other configurations could be used to generate an appropriate signal on the V-sense line that would serve the same function. In operation, then, the pulse 70 is generated whenever the amplified V-channel signal exceeds the threshold $V_T$, and is not generated when the signal is less than the threshold $V_T$. Advantageously, the value of the threshold $V_T$ may be a programmed value within the pacemaker which can be programmably set in order to adjust the sensitivity of this sense circuit to a desired level.

While the invention described herein has been described with reference to a particular embodiment and application thereof, numerous variations and modifications could be made thereto by those skilled in the art without departing from the spirit and scope of the invention as claimed. For example, it is to be understood that the circuits depicted in FIGS. 4A, 5A and 6A are only simplified functional circuits. Those skilled in logic design could readily fashion numerous alternative circuits that would serve the functions described. The present invention as claimed hereafter is thus intended to cover all such functionally-equivalent alternative circuits.

What is claimed is:

1. A method of automatically generating an adjustable blanking period in a first prescribed channel of a dual chamber pacemaker, said dual chamber pacemaker having two channels: a first channel having means for delivering stimulation pulses to a first chamber of a heart; and a second channel having means for delivering stimulation pulses to, and means for sensing electrical activity within, a second chamber of the heart, the sensing means of the second channel also being able to sense electrical activity that originates within the first chamber of the heart yet is detectable in the second chamber of the heart as crosstalk; said method comprising the steps of:

(a) initiating a basic blanking interval in the second channel of said pacemaker coincident with the delivery of a stimulation pulse in the first channel, said basic blanking interval comprising a first fixed absolute refractory portion followed by a second relative refractory portion;

(b) disabling the sensing means of the second channel during the first fixed absolute refractory portion of the basic blanking interval, whereby no electrical activity of any kind is sensed by said sensing means during said first fixed absolute refractory portion;

(c) enabling the sensory means of the second channel during the second relative refractory portion of the blanking interval;

(d) restarting said basic blanking interval in response to the first occurrence of any electrical activity sensed by the sensing means of the second channel during the second relative refractory portion, said adjustable blanking period comprising the cumulative sum of said first basic blanking interval plus any restarted blanking intervals; and (e) terminating said adjustable blanking period in the second channel in response to the earliest occurrence of either (i) the conclusion of the second relative refractory portion without the occurrence of any sensed electrical activity to restart the basic blanking interval, or (2) the conclusion of a prescribed maximum blanking period, said prescribed maximum blanking period being initiated at the delivery of the stimulation pulse in the first channel.

2. The method as set forth in claim 1 wherein said second channel of said dual chamber pacemaker comprises a ventricular channel, and said first channel comprises an atrial channel, whereby said method is for automatically generating a ventricular blanking period initiated by the generation of an atrial stimulation pulse.

3. The method as set forth in claim 1 wherein said second channel of said dual chamber pacemaker comprises an atrial channel, and said first channel comprises a ventricular channel, whereby said method is for automatically generating an atrial blanking period initiated by the generation of a ventricular stimulation pulse.

4. The method as set forth in claim 1 wherein step (d) comprises immediately restarting said basic blanking interval at the first occurrence of any electrical activity sensed by the sensing means of the second channel during the second relative refractory portion, said adjustable blanking period thereby comprising the cumulative sum of the first fixed absolute refractory portion of the first basic blanking interval, that portion of the second relative refractory portion of the first basic blanking interval prior to the occurrence of the sensed electrical activity, the first fixed absolute refractory portion of any restarted blanking intervals, and those portions of the second relative refractory portion of any restarted basic blanking intervals prior to the occurrence of any sensed electrical activity; unless said prescribed maximum blanking period first concludes, in which case said adjustable blanking period comprises said prescribed maximum blanking period.

5. The method as set forth in claim 1 wherein step (d) comprises restarting the first fixed absolute refractory portion of any restarted basic blanking interval at the conclusion of the first fixed absolute refractory portion of a preceding basic blanking interval, said adjustable blanking period thereby comprising the cumulative sum of the first fixed absolute refractory portion of the first basic blanking interval, the first fixed absolute refractory portions of any restarted basic blanking intervals, and the second relative refractory portion of the last basic blanking interval included in said adjustable blanking period; unless said prescribed maximum blanking period first concludes, in which case said adjustable blanking period comprises said prescribed maximum blanking period.

6. The method as set forth in claim 5 wherein step (a) includes defining said first fixed absolute refractory portion and said second relative refractory portion of said basic blanking interval to each include an integral number of clock periods of a basic clock signal, said adjustable blanking period thereby comprising, when not limited by said prescribed maximum blanking period, to an integral number of said clock periods.

7. The method as set forth in claim 6 wherein step (a) includes defining said first fixed absolute refractory portion of the basic blanking interval to include one clock period of said basic clock signal.

8. The method as set forth in claim 7 wherein step (a) further includes defining said second relative refractory portion of the basic blanking interval to include one clock period of said basic clock signal.

9. A method of automatically generating an adjustable blanking interval in a dual channel pacemaker, said adjustable blanking interval being used by a first channel of said pacemaker to blank out electrical activity present in said first channel during said blanking interval, which electrical activity, if any, is likely to be noise or crosstalk, said method comprising the steps of:

(a) generating a basic blanking interval in a first channel of said pacemaker whenever a stimulation pulse is generated in a second channel of said pacemaker, said basic blanking interval being divided into a first portion and a second portion;

(b) disregarding any electrical activity present in said first channel during said first portion of said blanking interval;

(c) retriggering said basic blanking interval in response to any electrical activity present in said first channel during said second portion of said basic blanking interval;

(d) repeating steps (b) and (c) for so long as electrical activity is present in said first channel during said second portion of any retriggered basic blanking interval; and (e) making said adjustable blanking interval equal to a value that varies as a function of the number of basic blanking intervals retriggered in step (c).

10. The method as set forth in claim 9 wherein step (e) comprises making said adjustable blanking interval equal to the cumulative sum of: (1) the first portion of the initial basic blanking interval; (2) the first portion of any retriggered basic blanking intervals; and (3) that part of the second portion of the initial basic blanking period and any retriggered basic blanking intervals that occurs prior to the presence of any electrical activity in said first channel.

11. The method as set forth in claim 10 wherein step (e) includes making said adjustable blanking interval equal to the shorter of said cumulative sum or a prescribed maximum blanking interval.

12. The method as set forth in claim 11 wherein step (a) includes dividing said basic blanking interval into substantially equal first and second portions.

13. The method as set forth in claim 9 wherein step (e) comprises making said adjustable blanking interval equal to the cumulative sum of: (1) the first portion of the initial basic blanking interval; (2) the first portion of any retriggered basic blanking intervals; and (3) the second portion of the last retriggered basic blanking interval.

14. The method as set forth in claim 13 wherein step (e) includes making said adjustable blanking interval equal to the shorter of said cumulative sum or a prescribed maximum blanking interval.

15. The method as set forth in claim 14 wherein step (a) includes synchronously dividing said basic blanking interval into said first and second portions using a clock signal, said first portion comprising a first prescribed number of clock signal periods, and said second portion comprising a second prescribed number of clock signal periods.

16. The method as set forth in claim 15 wherein step (a) further includes making the number of clock signal periods in said first and second portions of said basic blanking interval equal to the same number.

17. The method as set forth in claim 16 wherein step (a) includes making the number of clock signal periods in said first and second portions of said basic blanking interval equal to one.

18. An implantable dual chamber pacemaker comprising:
    first and second channels for allowing electrical contact to be made with first and second chambers of a heart, respectively;
    pacemaker control logic for generating a first trigger signal when a stimulation pulse is to be presented on said first channel;
    sensing means for sensing electrical activity on said second channel, said sensing means generating a sense signal when such electrical activity occurs;
    blanking interval means for automatically generating an adjustable blanking signal pulse having a variable width, said blanking interval means being responsive to said first trigger signal and said sense signal, said adjustable blanking signal pulse commencing at a time determined by said first trigger signal and ending at a time determined by said sense signal; and
    means responsive to said adjustable blanking signal pulse for rejecting any electrical activity sensed by said sensing means when said adjustable blanking signal pulse is present and for accepting any electrical activity sensed by said sensing means when said adjustable blanking signal pulse is absent.

19. The implantable dual chamber pacemaker set forth in claim 18 wherein said blanking interval means comprises means for generating a blanking pulse having a basic blanking interval, said basic blanking interval comprising two portions, a first absolute refractory portion, and a second relative refractory portion; and further wherein said sensing means is disabled during said first absolute refractory portion and is enabled during said second relative refractory portion; and still further wherein said blanking interval means further comprises means for retriggering said blanking pulse at such time that electrical activity is sensed by said sensing means during said second relative refractory portion, said adjustable blanking signal pulse thereby having an overall duration equal to the sum of the triggered basic blanking interval and the basic blanking intervals which are thereafter retriggered until no further sense signals are generated.

20. The implantable dual chamber pacemaker set forth in claim 19 wherein said absolute refractory portion of said basic blanking interval is substantially equal to said relative refractory portion.

21. The implantable dual chamber pacemaker set forth in claim 19, wherein said blanking interval means further comprises means for dividing said blanking pulse into the first absolute refractory portion and the second relative refractory portion and wherein said absolute refractory portion of said basic blanking interval is generated by said dividing means synchronously with a clock signal, said absolute refractory portion comprising an integral number of the periods of said clock signal.

22. The implantable dual chamber pacemaker set forth in claim 21 wherein said relative refractory portion of said basic blanking interval is also generated by said dividing means synchronously with a clock signal, said relative refractory portion comprising an integral number of the periods of said clock signal.

23. The implantable dual chamber pacemaker set forth in claim 22 wherein said absolute refractory portion and said relative refractory portion of said basic blanking interval each comprise one period of said clock signal.

24. Apparatus for automatically generating an adjustable blanking interval in a dual chamber pacemaker, said dual chamber pacemaker including first and second channels in which electrical activity may be sensed, said adjustable blanking interval being used in a first channel of said pacemaker to blank out electrical activity sensed in said first channel that may be noise or crosstalk originating in the second channel, said apparatus comprising:
    generating means for generating a basic blanking interval in said first channel whenever a stimulation pulse is generated in said second channel, said generating means dividing said basic blanking interval into a first portion and a second portion;
    first circuit means for disregarding any electrical activity present in said first channel during said first portion of said blanking interval;
    second circuit means for retriggering said basic blanking interval in response to any electrical activity present in said first channel during said second portion of said basic blanking interval;
    third circuit means for making said adjustable blanking interval equal to a value that varies as a function of the sum of a basic blanking interval and the basic blanking intervals which are thereafter retriggered by said second circuit means.

25. Apparatus as set forth in claim 24 wherein said third circuit means includes circuitry for making said adjustable blanking interval equal to a cumulative sum of: (1) the first portion of the initial basic blanking interval; (2) the first portion of any retriggered basic blanking interval; and (3) that part of the second portion of the initial basic blanking interval and any retriggered basic blanking interval that occurs prior to the presence of any electrical activity in said first channel.

26. Apparatus as set forth in claim 25 wherein said third circuit means further includes circuitry for making said adjustable blanking interval equal to the shorter of said cumulative sum or a prescribed maximum blanking interval.

27. Apparatus as set forth in claim 26 wherein said first and second portions of said basic blanking interval are of substantially equal duration.

28. Apparatus as set forth in claim 24 wherein said third circuit means includes circuitry for making said adjustable blanking interval equal to a cumulative sum of: (1) the first portion of the initial basic blanking interval; (2) the first portion of any retriggered basic blanking intervals; and (3) the second portion of the last retriggered basic blanking interval.

29. Apparatus as set forth in claim 28 wherein said third circuit means further includes circuitry for making said adjustable blanking interval equal to the shorter of said cumulative sum or a prescribed maximum blanking interval.

30. Apparatus as set forth in claim 29 wherein said generating means includes circuitry for synchronously dividing said basic blanking interval into said first and second portions using a clock signal, said first portion comprising a first prescribed number of clock signal periods, and said second portion comprising a second prescribed number of clock signal periods.

31. Apparatus as set forth in claim 30 wherein the number of clock signal periods in said first and second portions of said basic blanking interval are equal to the same number.

32. Apparatus as set forth in claim 31 wherein the number of clock signal periods in said first and second portions of said basic blanking interval is equal to one.

* * * * *